United States Patent [19]

McDonald

[11] Patent Number: 4,699,928
[45] Date of Patent: Oct. 13, 1987

[54] FLUOROALLYLAMINE DERIVATIVES

[75] Inventor: Ian A. McDonald, Pfulgriesheim, France

[73] Assignee: Merrell Dow Pharmaceuticals Inc., Cincinnati, Ohio

[21] Appl. No.: 928,672

[22] Filed: Nov. 6, 1986

Related U.S. Application Data

[63] Continuation of Ser. No. 745,127, Jun. 18, 1985, abandoned, which is a continuation-in-part of Ser. No. 630,556, Jul. 13, 1984, abandoned.

[51] Int. Cl.⁴ .................... A61K 31/35; C07C 93/08; C07C 149/42
[52] U.S. Cl. .................... 514/649; 514/651; 564/341; 564/347; 564/353
[58] Field of Search .............. 564/341, 346, 353; 514/651, 649

[56] References Cited

U.S. PATENT DOCUMENTS

| | | | |
|---|---|---|---|
| 3,079,403 | 2/1963 | Weinstock | 564/315 X |
| 3,542,870 | 11/1970 | Fourneau et al. | 564/347 |
| 3,657,244 | 4/1972 | Mentrup et al. | 564/362 |
| 4,031,245 | 6/1977 | Welstead, Jr. | 514/649 |
| 4,137,328 | 1/1979 | Cox et al. | 564/86 X |
| 4,454,158 | 6/1984 | Bey | 514/649 |

OTHER PUBLICATIONS

Burger, "Medicinal Chemistry", 2nd Ed. p. 599 (1960).

*Primary Examiner*—Robert V. Hines
*Attorney, Agent, or Firm*—Raymond A. McDonald

[57] ABSTRACT

Fluoroallylamine derivatives of the following Formula I are novel MAO-inhibitors and at low dose levels selectively inhibit MAO-B:

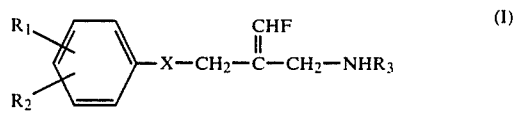

wherein:
$R_1$ and $R_2$ independently represent hydrogen, chlorine or fluroine;
$R_3$ represents hydrogen or $(C_1-C_4)$alkyl; and
X represents oxygen or sulfur.

They are useful for the treatment of depression and, co-administered with L-dopa, in the treatment of Parkinsonism.

8 Claims, No Drawings

FLUOROALLYLAMINE DERIVATIVES

This is a continuation application of our co-pending application Ser. No. 745,127, filed June 18, 1985, and now abandoned which application is a continuation-in-part application of our application Ser. No. 630,556, filed July 13, 1984, now abandoned.

This invention relates to novel chemical compounds and to pharmaceutical compositions and methods of treatment employing said compounds.

The class of compounds known as monoamine oxidase inhibitors (MAO inhibitors) has been employed in psychiatry for over 20 years for the treatment of depression [See Goodman and Gilman, *The Pharmacological Basis of Therapeutics*, 6th Ed., McMillan Publishing Co., Inc., N.Y., 1980, pages 427–430]. MAO Inhibitors currently used in the USA for treating depression are tranylcypromine (PARNATE, SKF), phenelzine (NARDIL, Parke-Davis), and isocarboxazid (MARPLAN, Roche). In addition, another MAO inhibitor, pargyline (EUTRON, Abbott), is available for the treatment of hypertension [See *Physicians' Desk Reference*, 34th Ed., Medical Economics Co., Oradell, N.J., 1980, pages 1327–1328 (phenelzine), pages 1466–1468 (isocarboxazid), pages 1628–1630 (tranylcypromine), and pages 521–522 (pargyline)]. In addition to being used in treating depression, MAO inhibitors can be employed to treat other psychiatric disorders, such as phobic anxiety states.

psychiatric disorders, such as depression, by increasing the concentration of one or more biogenic monoamines in the brain or sympathetic nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked, and the result is an increase in the availability of the monoamines for their physiological functions. Among the physiologically active monoamines which are known substrates for MAO are: (a) the so-called "neurotransmitter" monoamines, such as the catecholamines (e.g. dopamine, epinephrine, and norepinephrine) and the indoleamines (e.g. tryptamine and 5-hydroxytryptamine), (b) the so-called "trace" amines (e.g. o-tyramine, phenethylamine, tele-N-methylhistamine), and (c) tyramine.

The usefulness of the MAO inhibitors in treating depression is limited because the administration of such agents can potentiate the pharmacological actions of certain food substances or drugs leading to dangerous and sometimes lethal effects. For example, persons receiving a MAO inhibitor must avoid the ingestion of foods which have a high tyramine content (such as cheese) because the MAO inhibitor will block the metabolic degradation of tyramine in the gut to produce high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy cannot be given directly-acting sympathomimetic drugs (or precursors thereof) which are themselves substrates for MAO (e.g.dopamine, epinephrine, norepinephrine, or L-DOPA) or indirectly-acting sympathomimetic drugs (e.g. amphetamines or cold, hay-fever, or weight control preparations that contain a vasoconstrictor). The potentiation of the pressor effect of indirectly-acting sympathomimetic drugs is especially profound. This is because such drugs act peripherally primarily be releasing catecholamines in nerve endings, and the concentration of the liberated catecholamines will be dangerously elevated if the metabolic degradation of the catecholamines via MAO is blocked. In addition, a MAO inhibitor should not be used in combination with another MAO inhibitor or with hypotensive agents, dibenzazepine antidepressants, meperidine, CNS depressants, and anticholinergic agents.

Biochemical and pharmacological studies indicate that the MAO enzyme exists in two forms known as "MAO Type A" (MAO-A) and "MAO Type B" (MAO-B). The two forms differ in their distribution in body organs, in their substrate specificity, and in their sensitivity to inhibitors. In general, MAO-A selectively oxidizes the so-called "neurotransmitter" monoamines (epinephrine, norepinephrine, and 5-hydroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus they can be preferentially inhibited depending upon the chemical structure of the inhibitor and/or the relative concentrations of the inhibitor and the enzyme. The MAO inhibitors currently sold in the USA for the therapy of depression (tranylcypromine, phenelzine, and isocarboxazid) are not preferential in their action upon MAO. However, various chemical compounds are known in the art to be preferential inhibitors of MAO, the most important being clorgyline, pargyline, and L-deprenyl which are all reported to be clinically effective antidepressant agents. MAO-A is preferentially inhibited by clorgyline, while MAO-B is preferentially inhibited by pargyline and L-deprenyl. It should be observed that the "selectivity" of a MAO inhibitor arises because the inhibitor has a greater affinity for one form of the enzyme. Thus, the selectivity of an inhibitor for MAO-A or MAO-B in vivo will be dose-dependent, selectivity being lost as the dosage is increased. Clorgyline, pargyline, and L-deprenyl are selective inhibitors at lower dosages, but are not selective inhibitors at higher dosages. The literature concerning MAO-A and MAO-B and the selective inhibition thereof is extensive [See, for example, Goodman and Gilman, ibid, pages 204–205; Neff et al.,*Life Sciences*, 14, 2061 (1974); Murphy, *Biochemical Pharmacology*, 27, 1889 (1978); Knoll, Chapter 10, pages 151–171 and Sandler, Chapter 11, pages 173–181, in *Enzyme Inhibitors as Drugs*, M. Sandler, Ed., McMillan Press Ltd., London, 1980; Lipper et al., *Psychopharmacology*, 62, 123 (1979); Mann et al., *Life Sciences*, 26, 877 (1980); and various articles in *Monoamines Oxidase: Structure, Function, and Altered Functions*, T. Singer et al. Ed., Academic Press, N.Y., 1979].

Of the selective inhibitors of MAO, L-deprenyl is of interest since the "cheese effect" is not observed at the low dosages where preferential inhibition of MAO-B occurs [See Knoll, TINS, pages 111–113, May 1979]. This observation is not unexpected since the intestinal mucosa contains predominantly MAO-A which, because it is not inhibited, permits oxidation and removal of the ingested tyramine. The selectivity of L-deprenyl for MAO-B may account for its ability to potentiate L-DOPA for the treatment of Parkinson's disease without producing peripheral side effects, such as hypertension due to potentiation of pressor catecholamines [See Lees et al., Lancet, pages 791–795, Oct. 15, 1977 and Birkmeyer, Lancet, pages 439–443, Feb. 26, 1977].

In its first composition of matter aspect, this invention comprehends pharmacologically active fluoroallylamine derivatives of the following formula I:

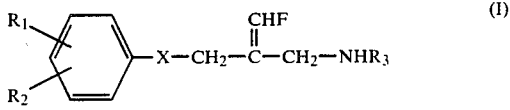

wherein:
$R_1$ and $R_2$ independently represent hydrogen, chlorine or fluorine;
$R_3$ represents hydrogen or ($C_1$–$C_4$) alkyl; and
X represents oxygen or sulfur,
and pharmacologically acceptable acid addition salts thereof.

The compounds of Formula I are pharmacologically active, being capable of inhibiting MAO in vitro and in vivo. They are useful for the treatment of psychiatric disorders, in particular depression, which are known to be responsive to MAO inhibitor therapy. For the treatment of depression, the compounds can be employed in a manner similar to that of the known clinically active MAO inhibitors, such as phenelzine and tranylcypromine.

Surprisingly, the compounds of Formula I are capable of preferentially inhibiting the B form of MAO in vitro and, at suitable low dosages in vivo, such compounds will inhibit MAO-B without substantially inhibiting MAO-A. At dosage levels where such compounds exert a selective effect on MAO-B, the compounds will not produce a marked "cheese effect". Hence, as with L-deprenyl, a known selective inhibitor of MAO-B, such compounds can be employed at suitable dosages for the treatment of depression, or for the potentiation of L-DOPA in the treatment of Parkinsonism, with a significantly decreased risk of producing side effects, such as the "cheese effect". The preferred compounds of Formula I showing selective inhibition of MAO-B are 2-phenoxymethyl-3-fluoroallylamine, 2-thiophenoxymethyl-3- fluoroallylamine and especially 2-(2', 4'-dichlorophenoxy)methyl-3-fluoroallylamine. These compounds, therefore, are the most preferred embodiments of Formula I.

As employed herein, the term "alkyl" contemplates both straight- and branched-chain alkyl groups. Straight-chain alkyl groups are preferred. Illustrative examples of ($C_1$–$C_4$) alkyl groups are methyl, ethyl, n-propyl, iso-propyl, n-butyl, iso-butyl, and tert-butyl. Methyl and ethyl are the most preferred alkyl groups.

When one or both of $R_1$ and $R_2$ is other than hydrogen, the relevant substituent group can be located at any of the available positions in the phenyl ring (i.e. in the ortho, para, or meta positions). When the phenyl ring is substituted by two substituent groups, the groups can be different but preferably are the same. Presently, 2,4 disubstitution is preferred.

It will be apparent to those skilled in the art that, because the compounds of Formula I contain a double bond, geometric isomerism is possible. It should be understood, therefore, that in Formula I, the fluorine atom can be oriented in the cis position or in the trans position. In naming compounds of Formula I herein, the prefixes "(E)" and "(Z)" are used in the conventional manner to indicate the stereochemistry at the double bond. If no stereochemical designation is given, both the substantially pure isomers, or mixtures thereof, are meant.

Presently preferred compounds of Formula I are those in which $R_3$ represents hydrogen. The more preferred compounds of Formula I are those wherein $R_3$ represents hydrogen and $R_1$ $R_2$ independently represent hydrogen or chlorine. It is also preferred that X represents oxygen.

Illustrative examples of the compounds of Formula I are:
2-(2'-chlorophenoxy)methyl-3-fluoroallylamine,
2-(4'-chlorophenoxy)methyl-3-fluoroallylamine,
2-(4'-fluorophenoxy)methyl-3-fluoroallylamine,
2-thiophenoxymethyl-3-fluoroallylamine,
2-(2',4'-dichlorophenoxy)methyl-3-fluoroallylamine,
2-(2',4'-dichlorothiophenoxy)methyl-3-fluoroallylamine,
2-(5'-chloro-3'-fluorophenoxy)methyl-3-fluoroallylamine,
2-(2'chlorothiophenoxy)methyl-3-fluoroallylamine,
2-(4'-fluorothiophenoxy)methyl-3-fluoroallylamine, 2-phenoxymethyl-3-fluoroallylamine,
2-(2'-chloro-4'-fluorothiophenoxy)methyl-3-fluoroallylamine, In its method of use aspect, the present invention provides a method for treating depression which comprises administering to a depressed patient an effective amount of a compound of Formula I or a pharmacologically acceptable acid addition salt thereof.

For pharmacological use, the compounds of Formula I may be administered in the form of an acid addition salt of a non-toxic organic or inorganic acid. Appropriate salts are those formed, for example, from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic.

When employed to treat depression, the effective dosage of the compounds of Formula I will vary according to the particular compound being employed, the severity and nature of the depression and the particular subject being treated. In general, effective results can be achieved by administering a compound at a dosage level from about 5 mg to about 100 mg per day, given systemically. Therapy should be initiated at lower dosages, the dosage thereafter being increased until the desired effect is obtained.

At dosage levels set forth above, the compounds of Formula I will, in general, inhibit both forms of MAO. However, at lower dosage levels, they will preferentially inhibit MAO-B and have a decreased risk of producing the "cheese effect". Thus, for example, 2-(2'4'-dichlorophenoxy)methyl-3-fluoroallylamine, 2-phenoxymethyl-3-fluoroallylamine, or 2-thiophenoxy-3-fluoroallylamine will selectively inhibit MAO-B at a systemic dosage range of about 0.1 mg to about 5 mg per day. At this dosage range, the risk of adverse reaction from the "cheese effect" will be substantially reduced or eliminated.

The active compounds of this invention can be administered in various manners to achieve the desired effect. The compounds can be administered alone or in combination with pharmaceutically acceptable carriers or diluents, the proportion and nature of which are determined by the solubility and chemical properties of the compound selected, the chosen route of administration, and standard pharmaceutical practice. The compounds may be administered orally in solid dosage forms, e.g. capsules, tablets, powders, or in liquid forms, e.g. solutions or suspensions. The compounds may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stablizing, solubilizing, or suspending agents. Parenteral preparations are sterile aqueous or nonaqueous solutions or suspensions which may contain certain various preserving, stabilizing, buffering, solubilizing, or suspending agents. If desired, additives, such as saline or glucose may be added to make the solutions isotonic.

The amount of active compound administered will vary and can be any effective amount. Unit doses of these compounds can contain, for example, from about 5 mg to about 100 mg of the compounds and may be administered, for example, one or more times daily, as needed.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction such as 5 ml (teaspoon) quantity of a liquid or a half or quarter of a scored tablet, of the multiple dose form.

In the composition aspect of the invention, there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefore. A carrier or diluent may be solid, semi-solid, or liquid material which serves as a vehicle, excipient, or medium for the active ingredient. Suitable diluents or carriers are well known per se. The pharmaceutical formulations may be adapted for enteral or parenteral use and may be administered to the patient in the form of tablets, capsules, suppositories, solutions, suspensions, or the like.

In the specific Examples included hereinbelow, illustrative examples of suitable pharmaceutical formulations are described.

The compounds of Formula I in which $R_3$ represents hydrogen can be obtained by reaction in manner known per se between an amino-protected derivative of the corresponding 1-fluoro-2-bromomethyl-3-aminopropene of the following Formula II and the corresponding phenol or thiophenol of the following Formula III and subsequent removal of the amino protecting group.

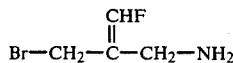
(II)

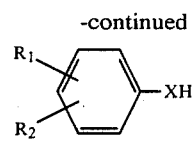

In Formulae II and III, $R_1$ and $R_2$ are as defined in connection with Formula I. The reaction is carried out under anhydrous conditions in the presence of a strong base, especially sodium hydride or butyl lithium, in an aprotic solvent, especially tetrahydrofuran. Usually, the reaction will proceed at room temperature.

Both amino hydrogen atoms of the 1-fluoro-2-bromomethyl-3-aminopropene must be protected during reaction with the phenol or thiophenol. Preferably, the protecting group is phthaloyl and conveniently the 1-fluoro-2-bromomethyl-3-phthalimidopropene is prepared directly by bromination in manner known per se of the corresponding 1-phthalimido-2-methyl-3-fluoro-2-propene of the following Formula IV.

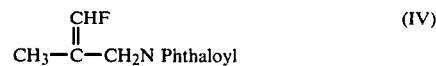
(IV)

Conveniently, the bromination is carried out using N-bromosuccinimide as the brominating agent.

The compounds of Formula IV can be obtained in manner known per se by treating the corresponding 2-methyl-3-fluoroallyl alcohol of the following Formula V with phthalimide in the presence of a triarylphosphine or trialkylphosphine and diethyl azodicarboxylate in an aprotic solvent, especially tetrahydrofuran or dioxane.

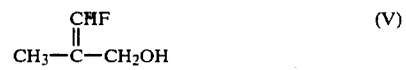
(V)

The compounds of Formula V can be obtained in manner known per se by reduction of the corresponding ethyl 2-methyl-3-fluoroacrylate of the following Formula VI

(VI)

Suitably, the reducing agent employed is diisobutylaluminium hydride in hexane, tetrahydrofuran, diethyl ether or dichloromethane or mixtures thereof at a reaction temperature of 0° to −75° C.

The compounds of Formula VI can be obtained in manner known per se by selectively hydrolyzing the t-butyl ester group of the corresponding t-butyl 2-difluoromethyl-2-carbethoxyalkanoate of the following Formula VII and subsequently decarboxylating the resultant 2-difluoromethyl-2-carbethoxyalkanoic acid of the following Formula VIII by treatment with a base.

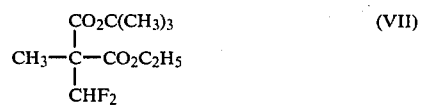
(VII)

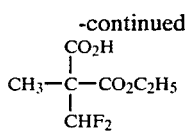

(VIII)

Suitably, the selective hydrolysis is carried out by treatment with an acid, preferably trifluoroacetic acid. The decarboxylation also eliminates one of the two fluorine atoms of the difluoromethyl moiety to provide the required acrylate of Formula VI. Suitably, a weak base, such as sodium bicarbonate, is employed to prevent excess base reacting with the double bond.

The compounds of Formula VII can be prepared by conventional difluoromethylation of the corresponding t-butyl 2-carbethoxyalkanoate (which are known per se) using sodium tert-butoxide and reacting the resultant carbanion with chlorodifluoromethane.

The amino-protected product of the reaction between the amino-protected derivative of the compound of Formula II and the phenol or thiophenol of Formula III is converted into the required compound of Formula I by removal of the protecting group in manner known per se. When the protecting group is phthaloyl, the said product can be cleaved by heating with hydrazine in an organic solvent or by heating with a strong mineral acid or a mixture of hydrochloric and acetic acids.

Compounds of Formula I in which $R_3$ represents alkyl can be prepared from the corresponding primary amines of Formula I (i.e. $R_3$ represents hydrogen) by conventional N-alkylation methods. For example, N-ethyl derivatives ($R_3$ represents ethyl) can be obtained by treating the primary amine with benzaldehyde in a lower alcohol, e.g. ethanol, to form a Schiffs base, treating the Schiffs base with triethyloxonium tetrafluoroborate, and hydrolyzing the intermediate thus formed.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the base.

A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with an inorganic acid may be treated with sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated in the following non-limiting Examples in which all temperatures are specified in degrees Centigrade.

EXAMPLE 1

(z)-2-(2',4'-dichlorophenoxy)methyl-3-fluoroallylamine

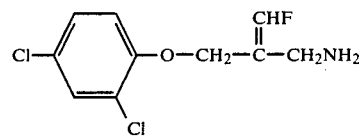

A. tert-Butyl 2-Carbethoxypropionate

A solution of diethyl methylmalonate (500 g) in ethanol (1000 ml) is treated with a clear solution of potassium hydroxide (116 g) in ethanol (1500 ml) for 16 hours. The mixture is concentrated to 1500 ml, filtered, then kept at −20° C. overnight by which time colorless needles form. These are filtered and dried to give a colorless product (335 g).

This product is dissolved in water (145 ml), cooled to about 5° C. and treated with concentrated hydrochloric acid (161 ml). After 1 hour, water is added and the product (254 g, 60% yield, colorless liquid) is isolated by ether extraction.

A portion (234 g) of this product is dissolved in anhydrous ether (600 ml), cooled in acetone-dry ice bath and treated consecutively with sulfuric acid (15 ml) and liquid isobutylene (600 ml). The reaction flask is firmly stoppered, the cooling removed and the solution is stirred for 6 hours. The solution is again cooled and treated with isobutylene (600 ml), then the reaction is left overnight. The solution is then poured into water (200 ml) containing potassium carbonate (115 g) and the mixture is extracted with ether. The ether extract gives tert-butyl 2-carbethoxypropionate (218 g, 67% yield) as a colorless liquid; b.p. 70° C. (oven)/0.05 mm Hg.

NMR (CCl₄): δ 1.24, t (J =7 Hz), 3H; 1.41, m, 12H; 3.17, q (J =7 Hz), 1H; 4.13, q (J =7 Hz), 2H.

B. tert-Butyl 2-Difluoromethyl-2-carbethoxypropionate

A slurry of sodium tert-butoxide (32.91 g) in dry tetrahydrofuran (THF) (200 ml) is stirred while a solution of tert-butyl 2-carbethoxypropionate (34.62 g) (prepared in Step A) in THF (100 ml) is added at a fast drop rate. The mixture is heated to 45° C. then the clear solution is treated with a fast stream of Freon 22 (Trade Mark) for about 5 min. The temperature rises rapidly and then falls at which time the Freon 22 addition is stopped. The heating bath is removed and the mixture is stirred for 1 hour, ice is added to reduce the temperature to about 20° C., then the mixture is washed several times with water. To ensure good separation of the layers, ether and small amounts of dilute aqueous hydrochloric acid are added when necessary. After drying the organic layer over magnesium sulfate the solvents are evaporated to leave a pale, orange oil (39.61 g, 92% yield). Generally, this material is sufficiently pure for the next step. Distillation of a small portion gives tert butyl 2-difluoromethyl-2-carbethoxypropionate as a colorless liquid; b.p. 90° C. (oven), 0.05 mm. Hg.

NMR (CCl₄): δ 1.26, t (J =7 Hz), 3H; 1.42, s, 12H; 4.19, q (J =7 Hz), 2H; 6.20, t (J =56 Hz), 1H.

Analysis for C₁₁H₁₈F₂O₄: Found: C, 52.47; H, 7.07%. Requires: C, 52.37; H, 7.19%.

C. (E)-Ethyl 2-Methyl-3-fluoroacrylate

A solution of tert-butyl 2-difluoromethyl-2-carbethoxypropionate (392 g) (prepared in Step B) in trifluoroacetic acid (TFA) (400 ml) is stirred at room temperature for several hours, then the excess TFA is removed by evaporation at reduced pressure. The residue is treated with carbon tetrachloride and re-evaporated.

The product is divided into two and each part is treated as follows:

A mixture of the crude acid, water (200 ml), chloroform (2000 ml) and sodium bicarbonate (250 g) is refluxed (bath temperature 70° C.) and vigorously stirred for 5.5 hours, then the mixture is allowed to cool to room temperature. The chloroform layer is separated, dried (magnesium sulfate), filtered and fractionally distilled at atmospheric pressure. The material with a boiling point range of 70°-115° C. was redistilled at reduced pressure to give essentially pure (E)-ethyl 2-methyl-3-fluoroacrylate (45 g, 22% yield) as a colorless liquid; b.p. 60°-70° C./80 mm. Hg.

NMR (CCl$_4$):$\delta$ 1.25, t (J =7 Hz), 3H; 1.79, d.d (J =4 Hz, 1.5 Hz), 3H; 4.13 t (J =7 Hz), 2H; 7.48, d.m (J =86 Hz), 1H.

D. (E)-2-Methyl-3-fluoroallyl Alcohol

A solution of diisobutylaluminium hydride (1318 ml) is added during 30 min to THF (1000 ml) cooled to $-55°$ to $-65°$ C., then a solution of (E)-ethyl 2-methyl-3-fluoroacrylate (58 g) (prepared in Step C) in THF (50 ml) is added over 15 min. The cooling bath is removed and the temperature is allowed to rise to 18° C. during 3 hours. Using an ice-salt bath, the solution is cooled and methanol (107 ml) is added so that the temperature is in the range $-10°$ to $+5°$ C., then after an additional 30 min water (175 ml) is added with the temperature at $-5°$ C. to $+5°$ C. The cooling is removed and the mixture is stirred for 1 hour and filtered. The filtrate is dried (magnesium sulfate), filtered and fractionally distilled at atmospheric pressure at first, then under reduced pressure. In this way pure (E)-2-methyl-3-fluoroallyl alcohol is obtained as a colorless liquid (19.0 g, 48% yield); b.p. 63° C./37 mm. Hg.

NMR (CDCl$_3$):$\delta$ 1.71, d.d (J =3 Hz, 1.5 Hz), 3H; 2.07, s, 1H; 3.98, d.d (J =4 Hz, 0.8 Hz), 2H; 6.60, d.m (J =84 Hz).

E. (E)-1-Phthalimido-2-methyl-3-fluoro-2-propene

A solution of (E)-2-methyl-3-fluoroallyl alcohol (prepared in Step D) (17.11 g), triphenylphosphine (49.80 g), diethyl azodicarboxylate (33.06 g) and phthalimide (27.93 g) in THF (500 ml) is stirred at room temperature overnight. The THF is evaporated and the oily residue is extracted three times with hexane giving a powdery solid which is subsequently extracted three times with ether. The combined extracts are evaporated and the residue (63 g) is purified by chromatography on silica gel (950 g) using a mixture of 20% diethyl ether/light petroleum. The major fraction is a colorless crystalline mass (28.6 g, 69% yield) which is essentially pure product. A small portion can be crystallized from hexane to give (E)-1-phthalimido-2-methyl-3-fluoro-2-propene as colorless plates: m.p. 57°-58° C.

NMR (CDCl$_3$): $\delta$ 1.67, d.d. (J =3.6 Hz, 1.8 Hz), 3H; 4.17, d (J =3.8 Hz), 2H; 6.77, d.m (J =84 Hz), 1H; centered at 7.82, m, 4H.

Analysis for C$_{12}$H$_{10}$FNO$_2$: *Found*: C, 65.71; H, 4.75; N, 6.26%. Requires: C, 65.75; H, 4.60; N, 6.39%.

F. (Z)-1-Fluoro-2-bromomethyl-3-phthalimidopropene

A mixture of 1-phthalimido-2-methyl-3-fluoro-2-propene (prepared in Step E) (2.09 g) and N-bromosuccinamide (1.78 g) in carbon tetrachloride (100 ml) was refluxed for 45 min. The cooled mixture is filtered and the filtrate is washed with water, dried and evaporated to leave an almost colorless oil. Chromatography (silica; 20% ether in light petroleum) followed by recrystallization of the major fractions from EtOAc/light petroleum gives:

(a) The less polar (Z)-1-fluoro-2-bromomethyl-3-phthalimdo-propene (1.00 g; 35% yield) as colorless needles; mp. 81°-83° C.

C$_{12}$H$_9$BrFNO$_2$: Found: C, 48.30; H, 3.14; N, 4.60%. Requires: C, 48.34; H, 3.04; N, 4.70%.

NMR (CDCl$_3$): $\delta$ 4.05, d (J =2 Hz), 2H; 4.33, d (J =3 Hz), 2H; 6.87, d (J =82 Hz), 1H; 7.62 to 7.95, m, 4H. (b) The more polar (E) 1-fluoro-2-bromomethyl-3-phthalimidopropene (0.25 g; 9% yield) as colorless needles; mp. 86°-87° C.

C$_{12}$H$_9$BrFNO$_2$: Found C, 48.39; H, 3.14; N, 4.66%. Requires C, 48.34; H, 3.04; N, 4.70%.

NMR (CDCl$_3$): $\delta$ 3.95, d (J =4 Hz), 2H; 4.53, d.d (J =2.5 Hz and less than 1 Hz), 2H; 6.85, d (J =80 Hz with additional fine coupling), 1H; 7.60 to 7.93, m, 4H.

G. (Z)-1-Fluoro-2-(2',4'-dichlorophenoxy)methyl-3-phthalimidopropene

Solid 1-fluoro-2-bromomethyl-3-phthalimidopropene (0.60 g) is added to a previously prepared mixture of 2,4-dichlorophenol (0.33 g) and sodium hydride dispersion (96 mg of 55–60% oil dispersion) in dimethylformamide (10 ml) at room temperature. Stirring is continued for 3 hours, then brine is added and the product is isolated by ether extraction. The extracted material is essentially pure (Z)-1-fluoro-(2',4'-dichlorophenoxy)-methyl -3-phthalimidopropene (0.67 g; 88% yield). A small portion is recrystallized from hexane/dichloromethane whereupon the analytical sample is obtained as colorless plates; mp. 115°-116° C.

C$_{18}$H$_{12}$Cl$_2$FNO$_3$: Found : C, 56.89; H, 3.25; N, 3.71%. Requires: C, 56.86; H, 3.18; N, 3.68%.

NMR (CDCl$_3$) : $\delta$ 4.37, d (J =3 Hz), 2H; 4.70, d (J =2.5 Hz), 2H; 6.80 to 7.23, m, 3H; 6.97, d (broadened, J =83 Hz), 1H; 7.75, m, 4H.

H. (Z)-2-(2',4'-dichlorophenoxy)methyl-3-fluorallylamine

A solution of (Z)-1-fluoro-2-(2',4'-dichlorophenoxy) methyl-3-phthalimidopropene (0.67 g) and hydrazine hydrate (0.13 g) in ethanol (20 ml) is refluxed for 3 hours. The ethanol is evaporated, the residue extracted with ether and the ether solution washed with dilute aqueous sodium hydroxide, then with water, dried and evaporated. The residue is treated with di-tert-butyl dicarbonate (0.44 g), chloroform (20 ml) and water (6 ml), with added sodium chloride (1 g), for 1.5 hours at reflux to give (Z)-N-t-butyloxycarbonyl-2-(2',4'-dichlorophenoxy)methyl-3-fluoroallylamine. Pure colorless needles (0.43 g) are obtained by silica chromatography using 15% EtOAC in light petroleum as eluant. Cleavage of the butyloxycarbonyl group (HCl/ether) gave (Z)-2-(2',4'-dichlorophenoxy)methyl-3-fluoroallylamine as its hydrochloride salt; colorless needles (0.30 g; 59% yield); mp 135°-136° C.

$C_{10}H_{11}Cl_3FNO$: Found : C, 41.78; H, 4.02; N, 4.74%. Requires : C, 41.91; H, 3.87; N, 4.89%.

NMR (CDCl$_3$) : δ 3.35, d (J =4 Hz), 2H; 4.80, d (J =2.5 Hz), 2H; 5.97, m, 1/2H; 6.90, 7.18, 7.35, ABC system ($J_{AB}$=10 Hz; $J_{BC}$=2 Hz; $J_{AC}$~0 Hz) overlapping 7.27, m, 3½ H.

EXAMPLE 2

The procedure of Steps G and H of Example 1 are repeated commencing with (E)-1-fluoro-2-bromomethyl-3-phthalimidopropene (prepared in Step F) instead of the (Z)-isomer to yield (E)-2-(2',4'- dichlorophenoxy)-methyl-3-fluoroallylamine, m.p. 104° C.

EXAMPLE 3

The procedure of Steps G and H of Example 1 are repeated using phenol instead of 2,4-dichlorophenol to yield (Z)-2-phenoxymethyl-3-fluoroallylamine m.p. 139°–140° C.

EXAMPLE 4

The procedure of Steps G and H of Example 1 are repeated using thiophenol instead of 2,4-dichlorophenol to yield (Z)-2-thiophenoxymethyl-3-fluoroallylamine, m.p. 164°–165° C.

EXAMPLE 5

The procedure of Steps G and H of Example 1 are repeated using p-fluorothiophenol instead of 2,4-dichlorophenol to yield the compound (Z)-2-(4'-fluorothiophenoxy) methyl-3-fluoroallylamine, m.p. 169° C.

EXAMPLE 6

The procedure of Steps G and H of Example 2 are repeated using thiophenol instead of 2,4-dichlorophenol to yield the compound (E)-2-thiophenoxymethyl-3-fluoroallylamine, m.p. 128° C.

EXAMPLE 7

N-methyl (Z)-2-(2',4'-dichlorophenoxy)methyl-3-fluoroallylamine

A mixture of (Z )-N-t-butyloxycarbonyl-2-(2',4'-dichlorophenoxy)methyl-3-fluoroallylamine (550 mg), prepared as in Step H of Example 1, dissolved in dimethylformamide (10 ml) is treated with sodium hydride (37 mg) for 30 minutes. A solution of methyl iodide (223 mg) in dimethylformamide (5 ml) is slowly added and the reaction mixture stirred overnight. Ether extractions followed by silica chromatography yields the protected N-methyl derivative as a colorless oil (180 mg). This oil is dissolved in HCl/ether whereupon N-methyl (Z)-2-(2',4'-dichlorophenoxy) methyl-3-fluoroallylamine is obtained as colorless needles, m.p. 154° C.

EXAMPLE 8

Inhibition of MAO—In vitro testing (A) The ability of a compound of Formula I to inhibit MAO can be determined in vitro by the method of A. Christmas et al., *Br. J. Pharmacol.*, 45, 490 (1972) in partially purified mitochondria from rat brain using $^{14}$C p-tyramine as the substrate. The MAO inhibitory activity of a compound is expressed as the "IC$_{50}$" value, which is the molar concentration required to produce 50% inhibition of the enzyme. The IC$_{50}$ values for certain compounds of Formula I were determined using the above-described method, and the results are set forth in Table I. For comparision, IC$_{50}$ values for clorgyline, L-deprenyl, and pargyline are also given. The data shown in Table I does not show selectivity of the compounds against MAO-A or MAO-B inhibitors, since $^{14}$C p-tyramine is a substrate for both forms of the enzyme.

TABLE I

| MAO Inhibitory activity - In vitro | |
|---|---|
| Compound (a) | IC$_{50}$ (moles) |
| (Z)—2-(2',4'-dichlorophenoxy)methyl-3-fluoroallylamine | 1.5 × 10$^{-7}$ |
| (Z)—2-phenoxymethyl-3-fluoroallylamine | 1 × 10$^{-6}$ |
| (Z)—2-thiophenoxymethyl-3 fluoroallylamine | 1 × 10$^{-6}$ |
| clorgyline | 1 × 10$^{-8}$ |
| L-deprenyl | 1 × 10$^{-7}$ |
| pargyline | 2 × 10$^{-6}$ |

(a) Tested as hydrochloride salt.

The data shown in Table I demonstrate that the compounds tested are potent inhibitors of MAO.

(B) The compounds of Formula I can be tested to determine whether or not the MAO inhibition follows time-dependent kinetics by the procedure described below:

Mitochondria are prepared from rat brain by homogenation in phosphate buffer (0.1 M, pH 7.2) followed by differential centrifugation. The mitochondria are suspended in the same buffer, the test compound is added at the desired concentration, and the system is incubated. At different time intervals, aliquots are taken and MAO activity is measured using $^{14}$C p-tyramine (a mixed substrate) as the substrate (See A. Christmas et al., supra). When (Z)-2-(2',4'-dichlorophenoxy)methyl-3 -fluoroallylamine was tested according to the above-described procedure, the MAO inhibitory activity increased as a function of time of incubation. The initial rate of decrease of activity increased with increasing concentration of inhibitor. The inhibition of MAO was shown to be irreversible since dialysis against phosphate buffer (24 hours) did not restore enzyme activity.

(C) The selectivity of a compound of Formula I with respect to inhibition of MAO-A and MAO-B can be determined by repeating the procedure of Part B and measuring the MAO activity using $^{14}$C 5-hydroxytryptamine (a preferred substrate for MAO-A) and $^{14}$C phenethylamine (a preferred substrate for MAO-B) as the substrate. The selectivity is expressed as the ratio of the inhibitory activity against MAO-B versus the inhibitory activity against MAO-A. In the case of (Z)-2-(2',4'-dichlorophenoxy)methyl-3-fluoroallylamine said ratio is 200, i.e. the compound was 200 times more selective for MAO-B than for MAO-A. Other compounds tested have equivalent or better selectivity as shown in Table II below:

TABLE II

| Compound | Ratio B:A |
|---|---|
| N—methyl (Z)—2-(2',4'-dichlorophenoxy) methyl-3-fluoroallylamine | 100 |
| (Z)—2-(4'-fluorothiophenoxy)methyl-3-fluoroallylamine | 100 |
| (E)—2-thiophenoxymethyl-3-fluoroallylamine | 100 |
| (Z)—2-thiophenoxymethyl-3-fluoroallylamine | 1,000 |

EXAMPLE 9

Inhibition of Mao—Ex Vivo

The ability of a compound of Formula I to inhibit MAO can be determined ex vivo by the following procedure:

The test compound is administered orally (p.o.) to 300–350 g male Sprague-Dawley rats (Charles River, France) and the animals are killed 18 hours after treatment. The brain, heart, liver and/or duodenum is removed and either a crude homogenate or a mitochondrial fraction, described in Example 5, Part (A), is prepared. MAO activity is determined in the homogenates using $^{14}C$ p-tyramine, as the substrate. Table III gives the results of the testing of (Z)-2-(2',4'-dichlorophenoxy)methyl-3-fluoroallylamine according to the above described procedure. Selectivity can be determined by repeating the above-described test using either $^{14}C$ p-hydroxytryptamine (for MAO-A) or $^{14}C$ phenethylamine (for MAO-B) as the substrate for determining the percentage inhibition.

V are obtained. In these tables the following abbreviations are used:
DA=dopamine,
HVA=homovanillic acid
NE=norepinephrine
DA=dopamine
DOPAC=dihydroxyphenylacetic acid
5-HT=5-hydroxytryptamine
5-HIAA=5-hydroxyindole-3-acetic acid

TABLE IV

EFFECT ADMINISTERED P.O. 18 HRS PREVIOUSLY ON BRAIN MONOAMINES AND THEIR METABOLITES.

|  | DA | DOPAC | HVA | NE | 5-HT | 5HIAA |
|---|---|---|---|---|---|---|
|  |  |  | ng/g S.E.M. |  |  |  |
| Control (saline) | 840 ± 27 | 80 ± 3 | 81 ± 3 | 369 ± 18 | 1156 ± 52 | 347 ± 8 |
| 1 mg/kg | 945 ± 35 (<0.05) | 75 ± 11 | 94 ± 15 | 386 ± 18 | 1218 ± 66 | 371 ± 19 |
| 2.5 mg/kg | 896 ± 31 | 70 ± 6 | 75 ± 7 | 409 ± 4 | 1119 ± 64 | 337 ± 15 |
| 5 mg/kg | 943 ± 21 (<0.02) | 65 ± 3 (<0.01) | 83 ± 7.2 | 415 ± 18 | 1340 ± 116 | 379 ± 10 (<0.05) |
| 10 mg/kg | 875 ± 16 | ± 3 (<0.005) | 53 ± 10 (<0.02) | 439 ± 15 (<0.02) | 1297 ± 100 | 343 ± 14 |
| 25 mg/kg | 1087 ± 29 (<0.001) | 54 ± 6 (<0.01) | 75 ± 8 | 496 ± 12 (<0.001) | 1623 ± 48 (<0.001) | 404 ± 12 (<0.005) | p values indicating that individual values differ from the relevant control values are presented in brackets.

TABLE III

| Dose (po) (mg/kg) | % Inhibition |  |  |  |  |  |  |  |
|---|---|---|---|---|---|---|---|---|
|  | Brain |  | Heart |  | Liver |  | Duodenum |  |
|  | (1) | (2) | (1) | (2) | (1) | (2) | (1) | (2) |
| 1 | 41 | 85 | 27 | 40 | 0 | 57 | 10 | 73 |
| 2.5 | 23 | 90 | 0 | 31 | 9 | 67 | 26 | 82 |
| 5 | 34 | 93 | 0 | 40 | 21 | 89 | 55 | 95 |
| 10 | 55 | 96 | 0 | 40 | 25 | 90 | 57 | 96 |
| 25 | 73 | 98 | 32 | 64 | 55 | 95 | 65 | 98 |

(1) using $^{14}C$—p-tyramine as substrate
(2) using $^{14}C$—phenethylamine as substrate It can be seen from Table III that the test compound produced preferential inhibition of MAO-B in the four tissues examined at the dose levels tested. Doses as low as 1 mg/kg p.o. produced greater than 80% inhibition of brain MAO-B with doses greater than 5 mg/kg being needed to inhibit MAO-A activity by more than 50%.

EXAMPLE 10

Inhibition of MAO—In vivo

The ability of a compound of Formula I to inhibit MAO can be determined in vivo using brain and heart samples obtained from the ex vivo study reported in Example 9. Monoamines and their deaminated metabolites were determined by HPLC with electrochemical detection by the method of J. Wagner et al, J. Neurochem. 38 1241–1254.

When (Z)-2-(2',4'-dichlorophenoxy)methyl-3-fluoroallylamine is tested according to the above-described procedure, the results given in Tables IV and V are obtained.

TABLE V

EFFECT ADMINISTERED P.O. 18 HRS PREVIOUSLY ON BRAIN MONOAMINES AND THEIR METABOLITES.

|  | NE | DOPAC | HVA | 5HT | 5HIAA |
|---|---|---|---|---|---|
| Control (saline) | 735 ± 100 | 78 ± 22 | 38 ± 9 | 808 ± 50 | 7 ± 1 |
| 1 mg/kg | 741 ± 56 | 56 ± 11 | 71 ± 6 (<0.02) | 1017 ± 79 | 16 ± 4 |
| 2.5 mg/kg | 762 ± 20 | 46 ± 12 | 53 ± 8 | 995 ± 108 | 7 ± 1 |
| 5 mg/kg | 875 ± 53 | 56 ± 7 | 60 ± 16 | 1018 ± 154 | 20 ± 6 |
| 10 mg/kg | 729 ± 58 | 62 ± 5 | 55 ± 3 | 850 ± 82 | 14 ± 2 |
| 25 mg/kg | 765 ± 50 | 87 ± 27 | 65 ± 4 (<0.02) | 685 ± 113 | 26 ± 4 (<0.02) | p values indicating that individual values differ from the relevant control values are presented in brackets.

As can be seen from Table IV significant reductions in dihydroxyphenylacetic acid and increases in dopamine were evident in the brain following the 5 mg/kg dose. Norepinephrine (NE) concentrations were increased significantly at the 10 and 25 mg/kg dose. Significant increases in 5-HT were obtained at the 25 mg/kg dose. However, as seen from Table V, no consistent changes in monoamines or their metabolites were obtained in the heart. These data are consistent with selectivity of action against MAO-B at the lower doses and a small degree of MAO-A inhibition occurring at the higher doses of the test compound.

EXAMPLE 11

The following test procedures can be employed to assess the potential of a compound of Formula I for producing the "cheese effect":

Male Sprague-Dawley rats (Charles River, France) weighing 240–347 g are given single doses of either 5, 10 or 25 mg/kg of the test compound by mouth. Eighteen hours later the animals are anaesthetized with pentobarbitone (60 mg/kg i.p.), in some instances pithed, and in all cases set up for recording heart rate and blood pressure by standard techniques. The effects of the test compound on intravenous tyramine were estimated in pithed rats using incremental doses of tyamine from 1.25 to 80 μg/kg injected every 7 minutes into a cannulated femoral vein. The effects on intraduodenal tyramine were assessed in anaesthetized rats by administering doses between 0.312 and 50 mg/kg at intervals of 15 min via a cannula placed in the duodenum. The results obtained for (Z)-2-(2',4'-dichlorophenoxy)methyl-3-fluoroallylamine are set forth in Table V.

As can be seen from Table VI, cardiovascular responses to tyramine injected intravenously were affected to only a small extent by 10 mg/kg given p.o. 18 h prior to testing. In two experiments, a clear 2-3 fold potentiation of tyramine was obtained following treatment with 25 mg/kg.

TABLE VI

Potentiation of heart rate response to p-tyramine

| Dose mg/kg | Route of administration of p-tyramine | Potentation of heart rate response to p-tyramine |
|---|---|---|
| (Z)—2-(2',4'-dichlorophenoxy)methyl-3-fluoroallylamine | | |
| 5 | i.d. | 1.5 fold |
| 10 | i.v. | none |
| 10 | i.d. | 2.4 fold |
| 25 | i.v. | 2.8 fold |
| 25 | i.d. | 2.0 fold |
| L-deprenyl | | |
| 0.1 | i.v. | 1.3 fold |
| 1.0 | i.v. | 2.2. fold |
| 0.1. | i.d. | no effect |
| 1.0 | i.d | 2.1. fold |
| clorgyline | | |
| 0.1. | i.v. | 5.2. fold |
| 0.1. | i.d. | 5.6 fold | i.v.: tyramine administered intraveously
i.d.: tyramine administered intradoudenally In the following Examples relating to pharmaceutical compositions, the term "active compound" is used to indicate the compound (Z)-2-(2',4'-dichlorophenoxy)methyl-3-fluoroallylamine. This compound may be replaced in these compositions by any other compound of the invention. Adjustments in the amount of medicament may be necessary or desirable depending upon the degree of activity of the medicament as is well known in the art.

EXAMPLE 12

An illustration composition of hard gelatin capsules is as follows:

| (a) Active compound | 5 mg |
|---|---|
| (b) Talc | 5 mg |
| (c) Lactose | 90 mg |

The formulation is prepared by passing the dry powders of (a) and (b) through a fine mesh screen and mixing them well. The powder is then filled into hard gelatine capsules at a net fill of 100 mg per capsule.

EXAMPLE 13

An illustrative composition for tablets is as follows:

| (a) Active compound | 5 mg |
|---|---|
| (b) Starch | 45 mg |
| (c) Lactose | 48 mg |
| (d) Magnesium stearate | 2 mg |

The granulation obtained upon mixing the lactose with the compound (a) and the part of the starch and granulated with starch paste is dried, screened, and mixed with the magnesium stearate. The mixture is compressed into tablets weighing 100 mg each.

EXAMPLE 14

An illustrative composition for an injectable suspension is the following 1 ml ampule for an intramuscular injection.

| | Weight percent |
|---|---|
| (a) Active compound | 0.5 |
| (b) Polyvinylpyrrolidone | 0.5 |
| (c) Lecithin | 0.25 |
| (d) Water from injection to make | 100.00 |

The materials (a)–(d) are mixed, homogenized, and filled into 1 ml ampule which are sealed and autoclaved 20 minutes at 121° C. Each ampule contains 5 mg per ml of the active compound.

I claim:

1. A fluoroallylamine derivative having the Formula I:

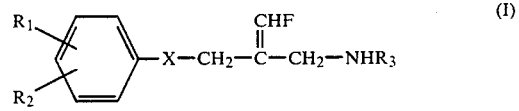

wherein:

$R_1$ and $R_2$ independently represent hydrogen, chlorine or fluorine;

$R_3$ represents hydrogen or ($C_1$-$C_4$) alkyl; and

X represents oxygen or sulfur, or a pharmacologically acceptable acid addition salt thereof.

2. A compound according to claim 1, wherein $R_3$ represents hydrogen.

3. A compound according to claim 1, wherein X represents oxygen.

4. A compound according to claim 1, wherein X is sulfur.

5. A compound according to claim 1, wherein $R_1$, $R_2$ and $R_3$ all represent hydrogen.

6. A compound according to claim 1, wherein $R_1$ and $R_2$ both represent chlorine atoms, said atoms being in the 2- and 4- positions of the phenyl ring.

7. A method of relieving the symptoms of depression in a patient in need thereof, which comprises administering to the patient a monoamine oxidase inhibiting amount of a fluoroallylamine derivative according to claim 1 or a pharmaceutically acceptable acid addition salt thereof.

8. An antidepressant pharmaceutical composition comprising an antidepressant effective amount of a fluoroallylamine derivative according to claim 1, or a pharmaceutically acceptable salt thereof, in combination with a pharmaceutically acceptable carrier or diluent.

* * * * *